United States Patent
Jarekrans

(10) Patent No.: US 6,743,624 B1
(45) Date of Patent: Jun. 1, 2004

(54) PROCESS FOR CONTINUOUS PURIFICATION AND CONCENTRATION OF LEUKOCYTES FROM BLOOD

(75) Inventor: Mats Jarekrans, Umeå (SE)

(73) Assignee: Bionative AB, Umeå (SE)

( * ) Notice: Subject to any disclaimer, the term of this patent is extended or adjusted under 35 U.S.C. 154(b) by 0 days.

(21) Appl. No.: 09/646,985

(22) PCT Filed: Mar. 23, 1999

(86) PCT No.: PCT/SE99/00452

§ 371 (c)(1),
(2), (4) Date: Nov. 17, 2000

(87) PCT Pub. No.: WO99/49016

PCT Pub. Date: Sep. 30, 1999

Related U.S. Application Data

(60) Provisional application No. 60/085,391, filed on May 14, 1998.

(30) Foreign Application Priority Data

Mar. 26, 1998 (SE) ................................ 9801029

(51) Int. Cl.[7] .............................................. C12N 5/00
(52) U.S. Cl. ..................... 435/325; 435/2; 435/283.1; 435/306.1; 435/372
(58) Field of Search ................... 435/2, 325, 372, 435/283.1, 306.1, 70.5

(56) References Cited

U.S. PATENT DOCUMENTS

| | | |
|---|---|---|
| 4,294,824 A | 10/1981 | Jones et al. |
| 4,938,876 A | 7/1990 | Ohsol |
| 5,785,869 A * | 7/1998 | Martinson et al. ............. 435/2 |

OTHER PUBLICATIONS

"*Methods in Enzymology*", Kari Cantell et al., 1981, vol. 78, pp. 29 to 38.
"*Methods in Enzymology*", Kari Cantell et al., 1981, vol. 78, pp. 499 to 505.

* cited by examiner

*Primary Examiner*—David Saunders
(74) *Attorney, Agent, or Firm*—Burns, Doane, Swecker & Mathis, L.L.P.

(57) ABSTRACT

Process and apparatus for the continuous purification and concentration of leukocytes from blood, characterized in that said process comprises the following steps: (a) seperating plasma from the blood by filtration in order to achieve a filtered buffy coat fraction; (b) adding an aqueous solution, which is hypotonic in relation to plasma, to the buffy coat fraction from step (a), in order to achieve lysation of erythrocytes contained in the buffy coat fraction; (c) mixing the buffy coat fraction and the aqueous hypotonic solution from step (b) in a mixing device; (d) leading the mixture from step (c) through a retention vessel; (e) leading the mixture from step (d) through a centrifuge in order to seperate the leukocytes; (f) collecting the separated leukocytes from step (e).

18 Claims, 2 Drawing Sheets

PROCESS FOR CONTINUOUS PURIFICATION AND CONCENTRATION OF LEUKOCYTES FROM BLOOD

Figure 1:
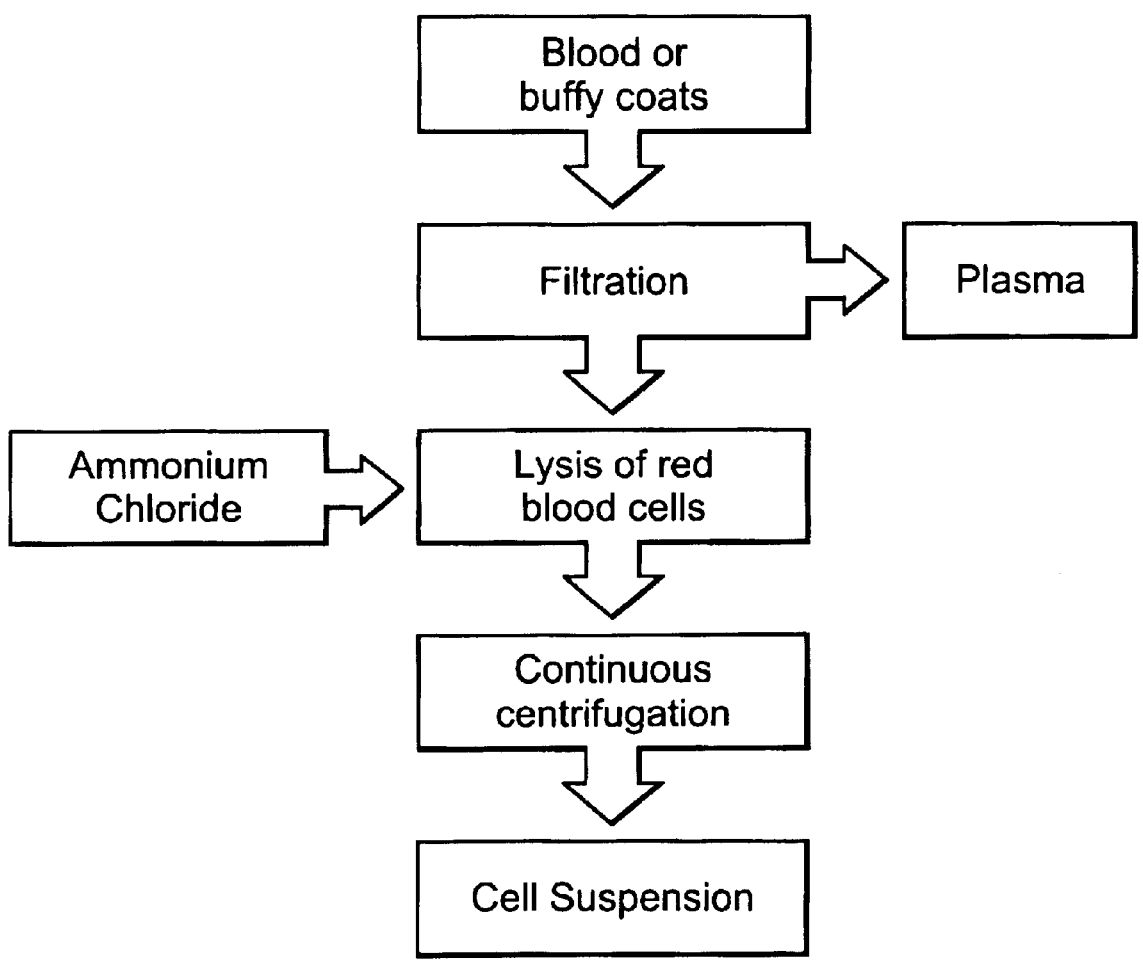

This application claims the benefit of provisional application Ser. No. 60/085,391 filed May 14, 1998.

FIELD OF THE INVENTION

The present invention relates to a new process and apparatus for continuous purification and concentration of leukocytes from blood, preferably buffy coats. The leukocytes are used in the production of interferon.

PRIOR ART

Interferons constitute an endogenously produced immunologically active group of small proteins, which act as a natural defence against viral infections. They are synthesised and secreted by vertebrate cells following a virus infection. Interferons bind to the plasma membrane of other cells in the organism and induce an antiviral state in them by enhancing the production of three enzymes: an oligonucleotide synthetase, an endonuclease, and a kinase. In modern medical care, pharmaceutical compositions containing interferons are administered as a regimen against infections, specially viral infections, but also to generally boost the patient's immunological defence systems.

Interferons are presently manufactured via three different routes: recombinant, cell-line derived and human leukocyte derived. The human leukocyte derived interferon products can further be divided in partially purified and highly purified products. The present application concerns in particular highly purified human leukocyte interferon.

The large scale production of human leukocyte derived interferon is generally performed according to the process outlined by Kari Cantell et al. 1981 (Cantell, K., Hirvonen, S., Kauppinen, H-L. and Myllyla, G., Production of interferon in human leukocytes from normal donors with the use of Sendai virus, in *Methods in Enzymology* vol 78, p. 29–38, and Cantell, K., Hirvonen, S. and Koistinen, V., Partial purification of human leucocyte interferon on a large scale, in *Methods in Enzymology*, vol 78, p.499–505.) The process according to Cantell can be summarised as follows: Pooled buffy coats from healthy donors are suspended in cold 0.83% $NH_4Cl$ and centrifuged. In this step the leukocytes are purified and separated from other blood cells. Approximately 30% of the leukocytes are lost. The leukocytes are collected and incubated in modified Eagle's minimum essential medium (MEM). Further, the suspension is primed with priming interferon and then inoculated with Sendai virus, to initiate the production of interferon. The harvested crude interferon is then pooled and the interferon precipitated and purified further.

In production with blood an anticoagulant can be added to the blood to prevent clot formation, thereby maintaining the blood in a fluid state. When blood treated in this way is undisturbed, the cells gradually settle because they are denser than the plasma; the red cells go to the bottom, the white cells and platelets form a thin white layer (buffy coat) overlying the red cells, and the plasma appears in the upper portion of the container.

The leukocyte preparation steps are still mostly performed batch wise, using manually handled laboratory flasks and suitable equipment. Scale up has up to now been achieved by adding more flasks and centrifuges and naturally more personel, handling these flasks. The production of interferon according to the state of the art is thus plagued by the drawbacks, typical for labour intensive processes: high labour costs, low reproducibility, variations in yield etc. Nevertheless, most of the present processes have been focused on how to best utilise available laboratory equipment and methodology.

The present invention aims to overcome these drawbacks and to enable higher yield, better reproducibility and lower labour costs. Additionally, the invention aims to enable easier scale-up and GMP-verifiability of the process.

SUMMARY OF THE INVENTION

The present invention offers a solution to the above mentioned problems and shortcomings of conventional processes by introducing a process according to the attached claims. The inventive process has e.g. the advantages of being suitable for automation, thus improving the reproducibility, lowering the operator input needed and reducing labour costs. Further, the inventive process is easy to scale up and adapt to larger production volumes.

SHORT DESCRIPTION OF THE DRAWINGS

Figure 2:
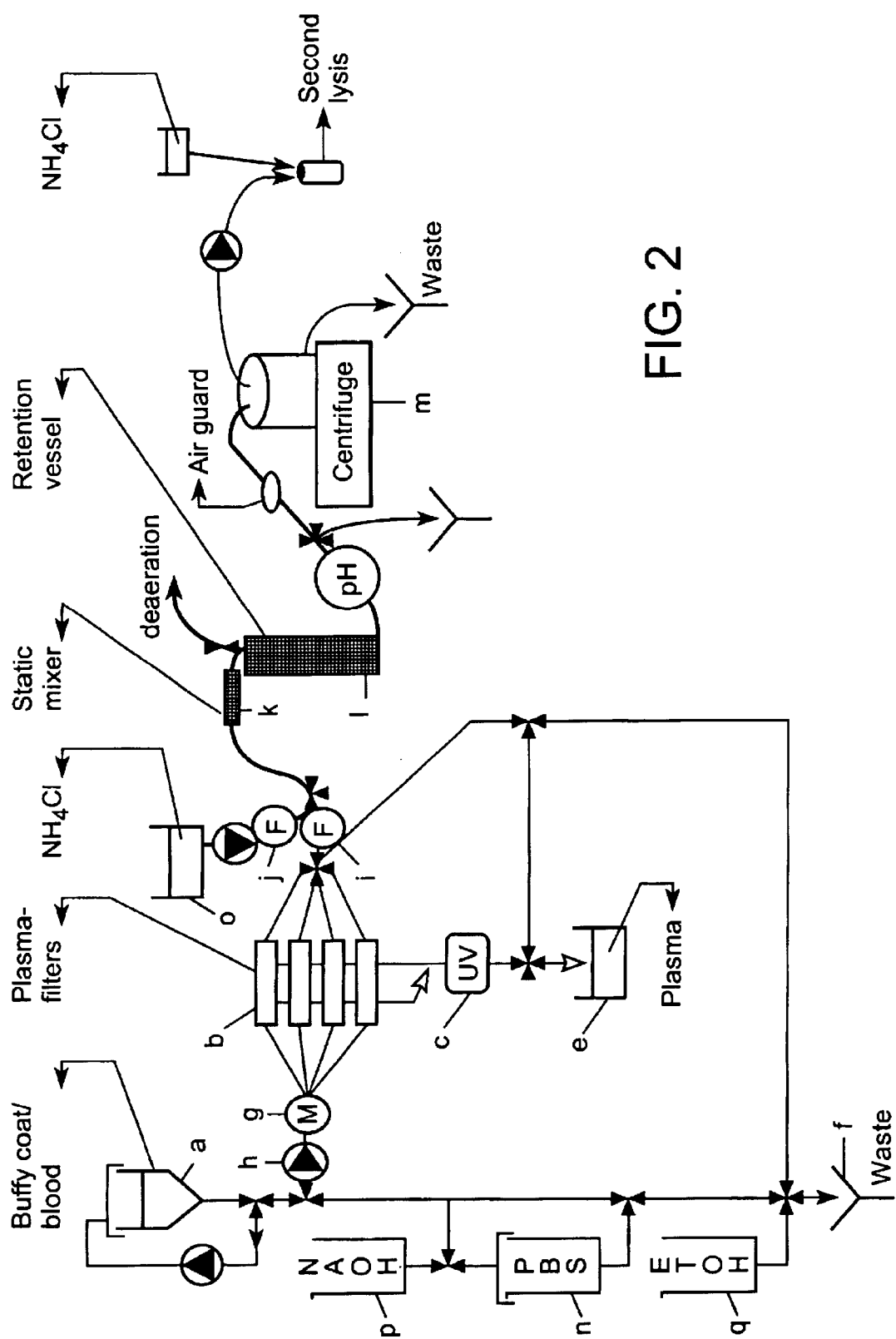

The invention will now be described in greater detail below with reference to the accompanying drawings in which FIG. 1 shows a block diagram showing the principles of a process according to the present invention;

FIG. 2 shows a schematic example of an automated leukocyte purification process according to the present invention.

DESCRIPTION OF THE INVENTION

The present inventor has surprisingly shown that a continuous and automated process can be used in the purification and concentration of leukocytes. According to the invention there is provided a process for the continuous purification and concentration of leukocytes from blood. The process comprises the following steps:

(a) separating plasma from the blood by filtration in order to achieve a filtered buffy coat fraction;

(b) adding an aqueous solution, which is hypotonic in relation to plasma, to the buffy coat fraction from step (a), in order to achieve lysation of erythrocytes contained in the buffy coat fraction;

(c) mixing the buffy coat fraction and the aqueous hypotonic solution from step (b) in a mixing device;

(d) leading the mixture from step (c) through a retention vessel;

(e) leading the mixture from step (d) through a centrifuge in order to separate the leukocytes;

(f) collecting the separated leukocytes from step (e).

According to a further aspect of the invention an apparatus is provided for continuous purification and concentration of leukocytes, from blood. The apparatus includes the following means:

(i) a membrane filter means for separating plasma from the blood by filtration in order to achieve a filtered buffy coat fraction;

(ii) a static mixer means for mixing the buffy coat fraction and an aqueous hypotonic solution in order to achieve lysation of erythrocytes contained in the buffy coat fraction;

(iii) a retention vessel means; and (iv) a centrifuge means in order to separate the leukocytes.

Referring to the block diagram in FIG. 1, the first step in the present process is a step of separating the plasma from blood by means of filtration. According to known processes plasma is usually separated from blood by centrifugation, which can result in a plasma fraction contaminated with lysed erythrocytes, which plasma fraction is of no further use. See e.g. U.S. Pat No. 4,294,824. The use of centrifugation in stead of filtration implies higher investment, more service and higher demands of sanitation and cleaning. In the present invention the plasma is separated from the blood by filtration and then the erythrocytes contained in the buffy coat obtained from the separation is lysed. According to a preferred embodiment of the invention the process starts with a commercially available buffy coat fraction obtained from a blood bank. This buffy coat fraction is separated from plasma contained therein by filtration. The plasma obtained is pure and can be further used. In the present invention it was surprisingly found that by separating plasma by filtration it was possible to obtain a continuous process that could be scaled up for large scale production. With conventional centrifuge separation in this step it was not possible to scale up the process. The centrifuge step, when scaled up, tended to crush the erythrocytes, thereby contaminating the buffy coat and the plasma. In large scale filtration the erythrocytes remained unchanged in the buffy coat and the separated plasma could be further used.

The filtration parameters in the process are balanced to produce, on one hand, a dense concentrated buffy coat fraction containing the leukocytes and, on the other hand, a pure plasma fraction, with as little discoloration as possible. The plasma fraction can be used as starting material in other processes since it is pure and contains no additives. According to one embodiment of the invention, the filtration step for separation of plasma and leukocytes, is performed with the aid of a membrane filter. Suitable filters have pore sizes within the interval of 0.1–1.0 $\mu$m, preferably within 0.4–0.6 $\mu$m. According to another embodiment the filtration is made through hollow fibres, suitable for use in the inventive process and as a part of the inventive apparatus or system.

In order to achieve lysation of the erythrocytes in buffy coat fraction, this fraction is mixed with a hypotonic solution in relation to plasma, e.g. aqueous ammonium chloride solution (e.g. 0–0.8% w/v) or, preferably 0.8%, but when using lower concentrations the lysation time has to be decreased. The flow of hypotonic solution is preferably twice the flow of the buffy coat fraction. Top ensure effective mixing, the mixture of the buffy coat fraction and e.g. the $NH_4Cl$ solution is lead through a static mixer and further to a retention vessel. The retention vessel is designed in a manner, considering the flow/volume ration, that a retention time of about 0.5–10 minutes is achieved, depending on the kind of hypotonic solution and the temperature used, and that the solution becomes homogenous in the entire vessel. The retention vessel is designated in a manner that a retention time of preferably 5–10 minutes is achieved when ammonium chloride solution is used, most preferably 10 minutes if cold 0.8% ammonium chloride solution is used.

Subsequently, the mixture of the buffy coat fraction and the $NH_4Cl$ solution is supplied to a continuous centrifuge in order to separate the leukocytes. The centrifuge can be a continuous or semi-continuous centrifuge of sanitary design and preferably a centrifuge adapted for sanitation without dismantling, Sanitation-In-Place (SIP) and also Clean-In-Place (CIP). In this step there is no problem to use a centrifuge for the separation, in a large scale process, as the erythrocytes have been removed by lysation.

Further processing may include a second erythrocyte lysis step. Finally, the purified and concentrated leukocytes, also called the cell suspension, are transferred to an incubation vessel, where the interferon production is induced by adding Sendai virus. Preferably the interferon production is carried out in a bioreactor. The advantages with using a bioreactor as the incubation vessel is the possibility to achieve better control of the incubation step, easier scale-up, facilitated Sanitation-In-Place, and Cleaning-In-Place. Together with the other steps described earlier in the text, this will constitute a more complex process better adapted to industrial manufacturing of interferon.

According to a preferred embodiment the blood used in the present invention is human blood.

EXAMPLES

Example 1

Plastic bags containing the buffy coat fraction are taken out from the ordinary production batch and emptied separately. Half of the amount of this fraction was emptied in a separate vessel (FIG. 2., a) and processed through the experimental process according to FIG. 2 and the other half according to the ordinary production process. In the experimental process, the plasma is separated by filtration through hollow fibres with appropriate fibre diameter and pore size (b). The filtered plasma is fractionated and the fractions with highest absorbency at 280 nm ($A_{280}$) are stored for later functional tests (results shown in Table 2.). The collection of plasma with highest absorbency is accomplished by measuring the absorbency at 280 nm online by means of a spectrophotometer (c) and when the absorbency has reached a predetermined value the valve (d) is automatically opened in the plasma vessel (e) direction. The spectrophotometer (c) is also utilised for measuring the amount of disrupted erythrocytes in the plasma. When erythrocytes are disrupted by e.g. mechanical forces they are lysed and the plasma becomes reddish due to the free haemoglobin. If the filtered plasma, for some reason becomes reddish it is discarded by setting a second criteria for the spectrophotometer (c) at about 410 nm. When the absorbency has reached a predetermined value at 410 nm, the valve (d) is automatically opened in the waste (f) direction.

Mechanical forces can, as mentioned earlier disrupt the erythrocytes. One way to disrupt the erythrocytes is to have to high feed pressure into the hollow fibres. Therefore, the feed pressure is automatically regulated by measuring the feed pressure with a pressure sensor (g) and to automatically adjust the pump (h) speed with respect to the feed pressure in order to keep the feed pressure constant at about 0.4 bars.

After the separation of plasma, the leukocyte fraction flows directly into a mixing chamber, a static mixer together with ammonium chloride. The flow of the leukocyte fraction is measured by a first flow meter (i). The flow of 0.8% (w/v) ammonium chloride fraction is measured by a second flow meter (j). Since the leukocyte fraction flow can change during the filtration step the flow of 0.8% (w/v) ammonium chloride fraction is automatically regulated with respect to the leukocyte fraction flow. The ammonium chloride flow is twice the leukocyte fraction flow. The blended solution is then entered into a static mixer (k) in order obtain a complete mixing of the two solutions. The mixed solution flows then continuously into the retention vessel (1). The retention time in the retention vessel is ten minutes which is the time for lysation according to the ordinary batch record. The lysate, which comes out from the retention vessel flows directly into the semi-continuous centrifuge (m), which was run at 3000 rpm. The centrifuge was then intermittently harvested. The harvested cells were lysed once more and suspended with some medium to form the cell suspension.

Certain amounts of the cell suspension are then added to 100 ml incubation flasks or to 3 liter laboratory fermentors in order to compare cells from the ordinary production process and the cells from the experimental process. The interferon from the labfermentors and 100 ml flasks are then analysed for interferon content by an ELISA method.

In the ordinary process the fractionation of plasma is achieved by centrifugation of the buffy coat fraction. The centrifugation is performed in one liter plastic bottles. The lysis occurs in a vessel, where the leukocyte fraction and the 0.8% (w/v) ammonium chloride solution are mixed and left to stand for ten minutes. The following centrifugation step is also carried out in one liter plastic bottles.

TABLE 1

Experimental yields: interferon

| | Amount add. (ml) | Cell conc. ($\times 10^7$ st/ml) | ELISA (IU/ml) | Yield/cell ($10^{-3}$ IU/cell) | Yield (%) | Yield/cell (%) | Tot. yield. |
|---|---|---|---|---|---|---|---|
| 961009 | | | | | | | |
| Exp.-cells | 1.5 | 0.8 | 32000 | 4 | 100 | 100 | 100% |
| Ref.-cells | 1.5 | 0.8 | 32000 | 4 | | | |
| 961023 | | | | | | | |
| Exp.-cells | 1.1 | 1 | 41000 | 4.1 | 85 | 90 | 155% |
| Exp.-cells | 1.1 | 1 | 47000 | 4.7 | | | |
| Ref.-cells | 2 | 1 | 52000 | 5.2 | | | |
| Ref.-cells | 2 | 1.1 | 51000 | 4.6 | | | |
| 961030 | | | | | | | |
| Exp.-cells | 1 | 0.8 | 42000 | 5.3 | 91 | 91 | 91% |
| Exp.-cells | 1 | 0.8 | 43000 | 5.4 | | | |
| Ref.-cells | 1 | 0.8 | 46000 | 5.8 | | | |
| Ref.-cells | 1 | 0.8 | 46000 | 5.8 | | | |
| Exp.-cells | 1.5 | 1.1 | 61000 | 5.5 | | | |
| Exp.-cells | 1.5 | 1.1 | 54000 | 4.9 | | | |
| Ref.-cells | 1.5 | 1.1 | 65000 | 5.9 | | | |
| Ref.-cells | 1.5 | 1.1 | 64000 | 5.8 | | | |
| 961114 | | | | | | | |
| Exp.-cells | 1 | 1.1 | 38000 | 3.5 | 84 | 82 | 84% |
| Exp.-cells | 1 | 1.1 | 37000 | 3.4 | | | |
| Exp.-cells | 1.5 | 1.7 | 56000 | 3.3 | | | |
| Exp.-cells | 1.5 | 1.7 | 56000 | 3.3 | | | |
| Ref.-cells | 1 | 1.1 | 42000 | 3.8 | | | |
| Ref.-cells | 1 | 1.1 | 46000 | 4.2 | | | |
| Ref.-cells | 1.5 | 1.6 | 70000 | 4.4 | | | |
| Ref.-cells | 1.5 | 1.6 | 64000 | 4 | | | |
| 961121 | | | | | | | |
| Exp.-cells | 1.5 | 1.1 | 58000 | 5.3 | 139 | 94 | 196% |
| Exp.-cells | 1.5 | 1.1 | 53000 | 4.8 | | | |
| Exp.-cells | 2 | 1.5 | 73000 | 4.9 | | | |
| Exp.-cells | 2 | 1.5 | 66000 | 4.4 | | | |
| Ref.-cells | 2 | 0.7 | 29000 | 4.1 | | | |
| Ref.-cells | 2 | 0.7 | 46000 | 6.9 | | | |
| Ref.-cells | 3 | 1.1 | 56000 | 5.1 | | | |
| Ref.-cells | 3 | 1.1 | 51000 | 4.6 | | | |
| 961127 | | | | | | | |
| Exp.-cells | 1.1 | 1.1 | 41000 | 3.7 | 128 | 92 | 193% |
| Exp.-cells | 1.1 | 1.1 | 47000 | 4.3 | | | |
| Exp.-cells | 1.5 | 1.7 | 69000 | 4.1 | | | |
| Exp.-cells | 1.5 | 1.7 | 69000 | 4.1 | | | |
| Ref.-cells | 1.5 | 0.8 | 32000 | 4 | | | |
| Ref.-cells | 1.5 | 0.8 | 36000 | 4.5 | | | |
| Ref.-cells | 2.5 | 1.2 | 53000 | 4.4 | | | |
| Ref.-cells | 2.5 | 1.2 | 56000 | 4.7 | | | |
| LabfermExp | 45 | 0.8 | 46000 | 5.8 | | | |
| LabfermRef | 84 | 0.8 | 40000 | 5 | | | |
| 961204 | | | | | | | |
| Exp.-cells | 1 | 0.8 | 30000 | 3.8 | 87 | 98 | 87% |
| Exp.-cells | 1 | 0.8 | 31000 | 3.9 | | | |
| Exp.-cells | 1.5 | 1.2 | 48000 | 4 | | | |
| Exp.-cells | 1.5 | 1.2 | 50000 | 4.2 | | | |
| Ref.-cells | 1 | 0.9 | 37000 | 4.1 | | | |
| Ref.-cells | 1 | 0.9 | 35000 | 3.9 | | | |
| Ref.-cells | 1.5 | 1.4 | 53000 | 4.4 | | | |
| Ref.-cells | 1.5 | 1.4 | 56000 | 4.1 | | | |
| Labferm Exp | 65 | 1.1 | 50000 | 4.5 | | | |
| Labferm Ref | 65 | 1.1 | 55000 | 5 | | | |

TABLE 1-continued

Experimental yields: interferon

| | Amount add. (ml) | Cell conc. (× 107 st/ml) | ELISA (IU/ml) | Yield/cell (10-3 IU/cell) | Yield (%) | Yield/cell (%) | Tot. yield. |
|---|---|---|---|---|---|---|---|
| 961206 | | | | | | | |
| Exp.-cells | 1.5 | 1 | 51000 | 5.1 | 116 | 116 | 78% |
| Exp.-cells | 1.5 | 1 | 48000 | 4.8 | | | |
| Exp.-cells | 2.25 | 1.5 | 83000 | 5.5 | | | |
| Exp.-cells | 2.25 | 1.5 | 79000 | 5.3 | | | |
| Ref.-cells | 1 | 1 | 40000 | 4 | | | |
| Ref.-cells | 1 | 1 | 50000 | 5 | | | |
| Ref.-cells | 1.5 | 1.5 | 70000 | 4.7 | | | |
| Ref.-cells | 1.5 | 1.5 | 62000 | 4.1 | | | |
| 961211 | | | | | | | |
| Exp.-cells | 1.5 | 1.1 | 66000 | 6 | 106 | 89 | 106% |
| Exp.-cells | 1.5 | 1.1 | 61000 | 5.5 | | | |
| Exp.-cells | 2 | 1.4 | 88000 | 6.3 | | | |
| Exp.-cells | 2 | 1.4 | 86000 | 6.1 | | | |
| Ref.-cells | 1.5 | 0.9 | 61000 | 6.8 | | | |
| Ref.-cells | 1.5 | 0.9 | 67000 | 7.4 | | | |
| Rer.-cells | 2 | 1.2 | 79000 | 6.6 | | | |
| Ref.-cells | 2 | 1.2 | 74000 | 6.2 | | | |
| Labferm.Exp | 65 | 1 | 68000 | 6.8 | | | |
| Labferm.Ref | 65 | 1 | 64000 | 6.4 | | | |
| MEAN | | | | | 104 | 94 | 121 |
| STAND. DEV. | | | | | 20 | 10 | 47 |
| C.V. | | | | | 19% | 10% | 39% |
| NO. | | | | | 9 | 9 | ·9 |

Table 1

The Table shows the result from functional tests of cells from the process according to the invention in comparison to cells from an ordinary batch. Exp.-cells means cells obtained from the process according to the invention. Ref.-cells means cells from an ordinary batch prepared from buffy coats from the same blood centre and the same day. LabfermExp means cells obtained from the process according to the invention but the test is performed in larger scale (3 liter) than Exp.-cells. LabfermRef means cells from an ordinary batch prepared from buffy coats from the same blood centre and the same day invention but the test is performed in larger scale 3 liter) than Ref.-cells. Amount add. means that different amounts of cell suspension have been added in order to achieve different cell concentrations for the functional test. Cellconc. is the measured cell concentration after addition of the amount of cells. ELISA is the result expressed in the amount of intereferon-alpha produced by the different cells per millilitre. Yield/cell is the result expressed in the amount of intereferon-alpha produced by the different cells per cell. Yield is the average result in percentage expressed in the amount of intereferon-alpha produced per millilitre by the Exp.cells/LabfermExp in comparison with the Ref.-cells/LabfermRef. Yield/cell II is the average result in percentage expressed in the amount of intereferon-alpha produced per cell by the Exp.cells/LabfermExp in comparison with the Ref.-cells/LabfermRef. Tot. yield is the total average amount of produced interferon-alpha by the Exp.cells/LabfermExp if the same amount of cells have been added. in percentage in comparison with the Ref.-cells/LabfermRef.

The results in Table 1 shows in average a better total yield with the inventive, Exp. cells in comparison with Ref.-cells. Since the two processes, Exp.-cell and Ref.-cell started with the same amount of cells and the volume of the final concentrated leukocyte cell suspension is the same for both processes, it is possible to calculate the recovery of cells from each process. When comparing the cell concentration in the trials performed 961121 and 961127 when the same amount of cell suspension have been added, it is obvious that the inventive process results in a higher cell recovery. Therefore, it is also possible to get more interferon from the inventive process since the yield and yield per cell is about the same.

The plasma recovered from the filtration step is used as a component in the incubation medium (EMEM). Before the plasma is added to the incubation medium, the immunoglobulin fraction is precipitated through addition of 25% (w/w) polyethylene-glycol (Macrogol 6000) solution. The polyethylene-glycol solution is prepared by solving 430 g into one liter distilled water.

In the ordinary process, an extra centrifugation step has to be performed (1600 rpm) on the plasma fraction in order to remove remaining cells.

The functional tests for plasma separated by hollow fibres was performed through adding this plasma instead of the ordinary plasma to the medium when incubating leukocytes in small scale, 100 ml flasks. Plasma was added to the incubation medium in equal amounts with respect to protein content, $A_{280}$ value. The interferon produced in these flasks were analysed by the ELISA-method and compared with ELISA-results from flasks ran with ordinary plasma.

TABLE 2

Experimental yields: plasma quality

| Plasma prep. | A 280 | Amount add. (ml) | Media add. (ml) | Cell conc. (× 107 st/ml) | ELISA (IU/ml) | Yield/cell (10-3 IU/cell) | Yield/cell (%) | Yield (%) |
|---|---|---|---|---|---|---|---|---|
| M-5296, Ref. | 25.6 | 1.6 | 40 | 1.2 | 63000 | 5.3 | 100 | 100 |
| M-5296, Ref. | 25.6 | 1.6 | 40 | 1.2 | 62000 | 5.2 | 100 | 100 |
| 961014 | 18.4 | 2.23 | 39.4 | 1.2 | 71000 | 5.9 | 115 | 115 |
| 961014 | 18.4 | 2.23 | 39.4 | 1.2 | 73000 | 6.1 | | |
| 961028 | 17.3 | 2.38 | 39.2 | 1.2 | 64000 | 5.3 | 109 | 109 |
| 961028 | 17.3 | 2.38 | 39.2 | 1.2 | 72000 | 6.0 | | |
| 961030 | 18.8 | 2.25 | 39.4 | 1.2 | 65000 | 5.4 | 102 | 102 |
| 961030 | 18.8 | 2.25 | 39.4 | 1.2 | 62000 | 5.2 | | |
| 961114 | 14.6 | 2.81 | 38.8 | 1.2 | 66000 | 5.5 | 102 | 102 |
| 961114 | 14.6 | 2.81 | 38.8 | 1.2 | 62000 | 5.2 | | |
| 961202 | 12.3 | 3.28 | 38.3 | 1.2 | 64000 | 5.3 | 106 | 106 |
| 961202 | 12.3 | 3.28 | 38.3 | 1.2 | 68000 | 5.7 | | |
| MEAN | | | | | | | 107 | 107 |
| STAND. DEV. | | | | | | | 6 | 6 |
| C.V. | | | | | | | 5% | 5% |
| NO. | | | | | | | 5 | 5 |

Table 2

The Table shows the result from functional tests of plasmas from the process according to the invention in comparison to plasma from an ordinary batch, M-5296, Ref. 961014, 961028, 961030, 961104 and 961202 are the dates when the filtered plasma were prepared. A 280 is the absorbency at 280 nm. Amount add. means that different amounts of plasma have been added in order to achieve the same protein content in the incubation medium. Media add. means the amount of incubation media used. Cellconc. is the measured cell concentration after addition of cells from the same cell suspension. ELISA is the result expressed in the amount of intereferon-alpha produced per millilitre. Yield/cell is the result expressed in the amount of intereferon-alpha per cell. Yield is the average result in percentage expressed in the amount of intereferon-alpha produced per millilitre by the cells incubated with different plasma prepared according to the inventive process in comparison with the plasma from an ordinary batch, M-5296. Yield/cell II is the average result in percentage expressed in the amount of intereferon-alpha produced per cell by the different plasma preparations in comparison with. Tot. yield is the total average amount of produced interferon-alpha by the cells incubated with different plasma preparations in percentage in comparison with the M-5296, Ref.

Example 2

Sanitation of the inventive process system was performed stepwise automatically: Flushing of the buffy coat vessel (a) and filters (b) with PBS (phosphate buffered saline) from vessel (n). Reversing the flow direction of PBS in the plasma filter Flushing of the static mixer (k), retention vessel (l) and centrifuge (m) with $NH_4Cl$ from vessel (o). Drainage of the whole system.

Cleaning of the whole system with 0.5 M NaOH from vessel (p) for at least half an hour. Drainage of the whole system.

The system is then filled with storage solution, 25% ethanol (v/v) from vessel (q).

Before use, the system is drained and then flushed with distilled water and then sterile PBS.

After sanitation, the system was disassembled at critical points and inspected visually to see that no cells, cell fragments etc. have been retained inside the system.

Samples were taken out on sterile PBS or on sterile water before each trial when the solution has passed the whole system or as indicated in table 3. The samples were analysed for bacterial counting (according to the European Pharmacopeia, 2nd Edition) and endotoxin determination (according to the European Pharmacopeia, 2nd Edition).

TABLE 3

Experimental results: sanitary status

| | Bact. (cfu/ml) | Endotox. (EU/ml) |
|---|---|---|
| 981009 | | |
| Wash sol.: PBS 961023 | <0.5 | <0.2 |
| Wash sol.: water 961030 | 0.5 | <0.2 |
| Wash sol.: water 961114 | <0.5 | <0.2 |
| Wash sol.: water, after hollow fibre | <0.5 | <0.2 |
| Wash sol.: water, after retention vessel 961121 | 1 | |
| Wash sol.: water, filtrate | <0.5 | ND |
| Wash sol.: water, after retention vessel 961127 | <0.5 | |
| Wash sol.: water 961204 | <0.5 | <0.2 |
| Wash sol.: water 961206 | <0.5 | ND |
| Wash sol.: water 961211 | <0.5 | ND |
| Wash sol.: water | <0.5 | ND |

No cells, cell fragments etc. were seen inside the system. Table 3 shows that the inventive system can be run under aseptic conditions and is suitable for CIP, that is cleaned in place.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A process for the continuous purification and concentration of leukocytes from a buffy coat fraction, characterized in that said process comprises the following steps:
   (a) separating plasma from the buffy coat fraction by filtration in order to achieve a filtered buffy coat fraction;
   (b) adding an aqueous solution, which is hypotonic in relation to plasma, to the filtered buffy coat fraction resulting from step (a), in order to achieve lysis of erythrocytes contained in the filtered buffy coat fraction;
   (c) mixing the filtered buffy coat fraction and the aqueous hypotonic solution from step (b) in a mixing device;
   (d) leading the mixture from step (c) through a retention vessel;
   (e) leading the mixture from step (d) through a centrifuge in order to separate the leukocytes;
   (f) collecting the separated leukocytes from step (e).

2. Process according to claim 1, characterized in that in step (b) the aqueous hypotonic solution is ammonium chloride.

3. Process according to claim 1, characterized in that the filtration is performed by leading the buffy coat fraction through a membrane filter with a pore size in the interval of 0.1–1.0 $\mu$m.

4. Process according to claim 3, characterized in that the filtration is performed by leading the buffy coat fraction through a membrane filter with a pore size in the interval of 0.4–0.6 $\mu$m.

5. Process according to claim 1, characterized in that the retention vessel is designed in a way resulting in a retention time for the mixture in step (d) of about 0.5–10 minutes.

6. Process according to claim 1, characterized in that the leucocytes collected in step (f) are subjected to a second lysis step.

7. Process according to claim 1, characterized in that the leukocytes collected in step (f) are incubated in a bioreactor for interferon production.

8. Process according to claim 1, characterized in that the plasma separated in step (a) is recovered.

9. Process according to claim 1, characterized in that the process is automatically operated and adapted for clean in place (CIP) cleaning and sanitation in place (SIP), wherein the CIP is performed by automatically cleaning the centrifuge, retention vessel and mixing device, as well as filters used in the filtration of step (a), by pumping cleaning solutions in the system; and the SIP is performed by sanitizing the centrifuge, retention vessel and mixing device, as well as filters used in the filtration of step (a), by a liquid or a gas which kills microorganisms, or heat.

10. Process according to claim 1, characterized in that the buffy coat fraction is derived from human blood.

11. Process according to claim 1, characterized in that in step (b) the aqueous hypotonic solution is ammonium chloride.

12. Process according to claim 1, characterized in that the plasma separated in step (a) is recovered.

13. An apparatus for continuous purification and concentration of leukocytes from a buffy coat fraction, characterized in that said apparatus includes the following means:
   (i) a membrane filter means for separating plasma from the buffy coat fraction by filtration in order to achieve a filtered buffy coat fraction;
   (ii) static mixer means for mixing the filtered buffy coat fraction and an aqueous hypotonic solution;
   (iii) a retention vessel means for achieving lysis of erythrocytes contained in the filtered buffy coat fraction;
   (iv) a centrifuge means for separating the leukocytes.

14. Apparatus according to claim 13, characterized in that the membrane filter means is a filter with a pore size in the interval of 0.1–1.0 $\mu$m.

15. Apparatus according to claim 13, characterized in that the membrane filter means is a filter with a pore size in the interval of 0.4–0.6 $\mu$m.

16. Apparatus according to claim 13, characterized in that the retention vessel means is designed in a way resulting in a retention time for the mixture in the retention vessel of about 0.5–10 minutes.

17. Apparatus according to claim 13, characterized in that the centrifuge is adapted to continuous separation of the leukocytes.

18. Apparatus according to claim 13, characterized in that said apparatus is equipped for cleaning and sanitation, which cleaning and sanitation does not require the dismantling of the equipment, so called clean in place (CIP) and sanitation in place (SIP).

* * * * *